US008147564B2

(12) United States Patent
Deconinck et al.

(10) Patent No.: US 8,147,564 B2
(45) Date of Patent: Apr. 3, 2012

(54) AGENT FOR DYEING AND/OR BLEACHING KERATIN FIBERS, COMPRISING COMPOSITION (A), ANHYDROUS COMPOSITION (B), AND AT LEAST ONE FATTY SUBSTANCE

(75) Inventors: Gautier Deconinck, Saint Gratien (FR); Caroline Goget, Paris (FR); Jean Cotteret, Maisons Laffite (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/976,093

(22) Filed: Dec. 22, 2010

(65) Prior Publication Data

US 2011/0155166 A1 Jun. 30, 2011

Related U.S. Application Data

(60) Provisional application No. 61/294,929, filed on Jan. 14, 2010.

(30) Foreign Application Priority Data

Dec. 22, 2009 (FR) ...................................... 09 59388

(51) Int. Cl.
*A61Q 5/10* (2006.01)
(52) U.S. Cl. ............. 8/405; 8/406; 8/410; 8/435; 8/604; 8/619
(58) Field of Classification Search .............. 8/405, 406, 8/410, 435, 604, 619
See application file for complete search history.

(56) References Cited

U.S. PATENT DOCUMENTS

| 3,100,739 | A | 8/1963 | Kaiser et al. |
| 3,369,970 | A | 2/1968 | McLaughlin et al. |
| 3,629,330 | A | 12/1971 | Brody et al. |
| 3,861,868 | A | 1/1975 | Milbrada |
| 4,138,478 | A | 2/1979 | Reese et al. |
| 4,170,637 | A | 10/1979 | Pum |
| 4,226,851 | A | 10/1980 | Sompayrac |
| 4,357,141 | A | 11/1982 | Grollier et al. |
| 4,366,099 | A | 12/1982 | Gaetani et al. |
| 4,488,564 | A | 12/1984 | Grollier et al. |
| 4,725,282 | A | 2/1988 | Hoch et al. |
| 4,826,681 | A | 5/1989 | Jacquet et al. |
| 4,845,293 | A | 7/1989 | Junino et al. |
| 5,021,066 | A | 6/1991 | Aeby et al. |
| 5,259,849 | A | 11/1993 | Grollier et al. |
| 5,364,414 | A | 11/1994 | Lang et al. |
| 5,817,155 | A | 10/1998 | Yasuda et al. |
| 6,010,541 | A | 1/2000 | De La Mettrie et al. |
| 6,074,439 | A | 6/2000 | De La Mettrie et al. |
| 6,129,770 | A | 10/2000 | Deutz et al. |
| 6,156,713 | A | 12/2000 | Chopra et al. |
| 6,165,444 | A | 12/2000 | Dubief et al. |
| 6,190,421 | B1 | 2/2001 | Rondeau et al. |
| 6,206,935 | B1 | 3/2001 | Onitsuka et al. |
| 6,238,653 | B1 | 5/2001 | Narasimhan et al. |
| 6,251,378 | B1 | 6/2001 | Laurent et al. |
| 6,260,556 | B1 | 7/2001 | Legrand et al. |
| 6,277,154 | B1 | 8/2001 | Lorenz |
| 6,277,155 | B1 | 8/2001 | De La Mettrie et al. |
| 6,365,136 | B1 | 4/2002 | Lauscher et al. |
| 6,423,100 | B1 | 7/2002 | Lang et al. |
| 6,447,552 | B1 | 9/2002 | Golinski |
| 6,645,258 | B2 | 11/2003 | Vidal et al. |
| 6,660,045 | B1 | 12/2003 | Hoeffkes et al. |
| 6,695,887 | B2 | 2/2004 | Cottard et al. |
| 6,800,098 | B1 | 10/2004 | Allard et al. |
| 7,135,046 | B2 | 11/2006 | Audousset |
| 7,153,331 | B2 | 12/2006 | Desenne et al. |
| 7,217,298 | B2 | 5/2007 | Legrand et al. |
| 7,285,137 | B2 | 10/2007 | Vidal et al. |
| 7,442,215 | B2 | 10/2008 | Audousset et al. |
| 7,458,993 | B2 | 12/2008 | Cottard et al. |
| 7,494,513 | B2 | 2/2009 | Kravtchenko et al. |
| 7,575,605 | B2 | 8/2009 | Legrand |
| 7,651,533 | B2 | 1/2010 | Legrand |
| 7,651,536 | B2 | 1/2010 | Cottard et al. |

(Continued)

FOREIGN PATENT DOCUMENTS

| CA | 1 268 421 | 5/1990 |
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |

(Continued)

OTHER PUBLICATIONS

Canterbery, P.R. et al., International Cosmetic Ingredient Dictionary and Handbook, vol. 1, p. 759 (2002).
Copending U.S. Appl. No. 12/003,321, filed Dec. 21, 2007.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.

(Continued)

*Primary Examiner* — Eiso Elhilo
(74) *Attorney, Agent, or Firm* — Finnegan, Henderson, Farabow, Garrett & Dunner, L.L.P.

(57) ABSTRACT

The present disclosure relates to an agent for dyeing and/or bleaching keratin fibers, comprising: composition (A) comprising at least one basifying agent, and anhydrous composition (B) comprising hydrogen peroxide and/or at least one hydrogen peroxide precursor, wherein composition (A) and/or composition (B) comprise at least one fatty substance not containing any carboxylic acid functional groups, such that the total amount of the at least one fatty substance not containing any carboxylic acid functional groups is present in the mixture of composition (A) and composition (B) in an amount greater than 20% by weight. The disclosure also relates to a process for treating human keratin fibers using this dyeing and/or bleaching agent, and a multi-compartment kit comprising this dyeing and/or bleaching agent in at least two parts.

22 Claims, No Drawings

U.S. PATENT DOCUMENTS

| | | | |
|---|---|---|---|
| 7,740,663 B2 | 6/2010 | De La Mettrie et al. | |
| 7,766,977 B2 | 8/2010 | Cottard et al. | |
| 7,799,095 B2 | 9/2010 | Mario et al. | |
| 2002/0189034 A1 | 12/2002 | Kitabata et al. | |
| 2003/0064494 A1 | 4/2003 | Kumar et al. | |
| 2003/0190297 A1 | 10/2003 | Narasimhan et al. | |
| 2003/0226217 A1 | 12/2003 | Bowes et al. | |
| 2004/0103488 A1 | 6/2004 | Yamashita et al. | |
| 2004/0105830 A1 | 6/2004 | Boswell et al. | |
| 2004/0172771 A1 | 9/2004 | Cottard et al. | |
| 2004/0181883 A1 | 9/2004 | Legrand et al. | |
| 2004/0221400 A1 | 11/2004 | Cotteret et al. | |
| 2004/0226110 A1 | 11/2004 | Legrand | |
| 2004/0235700 A1 | 11/2004 | Legrand et al. | |
| 2005/0129652 A1 | 6/2005 | Keller et al. | |
| 2005/0165705 A1 | 7/2005 | Lauper et al. | |
| 2005/0196367 A1 | 9/2005 | Ohta et al. | |
| 2006/0042023 A1 | 3/2006 | Machida | |
| 2006/0075580 A1 | 4/2006 | Chan et al. | |
| 2006/0137111 A1 | 6/2006 | Au et al. | |
| 2006/0242773 A1 | 11/2006 | Kravtchenko et al. | |
| 2006/0260071 A1 | 11/2006 | Legrand | |
| 2006/0265817 A1* | 11/2006 | Legrand | 8/405 |
| 2007/0006397 A1 | 1/2007 | Schmenger et al. | |
| 2007/0033743 A1 | 2/2007 | Kravtchenko | |
| 2007/0104672 A1 | 5/2007 | Decoster et al. | |
| 2007/0169285 A1 | 7/2007 | Narasimhan et al. | |
| 2007/0275927 A1 | 11/2007 | Philippe | |
| 2007/0277331 A1 | 12/2007 | Goldstein et al. | |
| 2008/0016627 A1 | 1/2008 | Cottard et al. | |
| 2008/0071092 A1 | 3/2008 | Vidal et al. | |
| 2008/0229512 A1 | 9/2008 | Syed et al. | |
| 2008/0256724 A1 | 10/2008 | Bolton et al. | |
| 2009/0007347 A1 | 1/2009 | Cottard et al. | |
| 2009/0060855 A1 | 3/2009 | Boche et al. | |
| 2009/0151086 A1 | 6/2009 | Brun | |
| 2009/0151087 A1 | 6/2009 | Mario et al. | |
| 2009/0158533 A1 | 6/2009 | Hercouet | |
| 2009/0162309 A1 | 6/2009 | Hercouet et al. | |
| 2009/0191142 A1 | 7/2009 | Hercouet et al. | |
| 2010/0162492 A1 | 7/2010 | Hercouet et al. | |
| 2010/0175705 A1 | 7/2010 | Hercouet et al. | |
| 2010/0186177 A1 | 7/2010 | Hercouet et al. | |
| 2010/0199441 A1 | 8/2010 | Hercouet et al. | |

FOREIGN PATENT DOCUMENTS

| | | |
|---|---|---|
| DE | 197 54 281 | 6/1999 |
| DE | 198 15 338 | 9/1999 |
| DE | 198 42 071 | 3/2000 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 449 512 | 8/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 047 841 | 4/2009 |
| EP | 2 072 034 | 6/2009 |
| EP | 2 072 035 | 6/2009 |
| EP | 2 072 036 | 6/2009 |
| EP | 2 198 842 | 6/2010 |
| EP | 2 198 843 | 6/2010 |
| EP | 2 198 849 | 6/2010 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| FR | 2 940 054 | 6/2010 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |

| | | |
|---|---|---|
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
Copending U.S. Appl. No. 12/976,124, filed Dec. 22, 2010.
Copending U.S. Appl. No. 12/976,150, filed Dec. 22, 2010.
Copending U.S. Appl. No. 12/976,173, filed Dec. 22, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language abstract of DE 198 42 071, dated Mar. 16, 2000.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
European Search Report for EP 10 19 5262, dated Apr. 1, 2011.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.

French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
French Search Report for FR 09/59388, dated Aug. 3, 2010.
French Search Report for FR 09/59391, dated Sep. 16, 2010.
French Search Report for FR 09/59433, dated Sep. 24, 2010.
French Search Report for FR 09/59434, dated Sep. 24, 2010.
International Search Report for PCT/FR2009/052617, dated Mar. 30, 2010.
LookChem, "Poly[(dimethyliminio)-1,1,6-hexanediylchloride (1:2)]," pp. 1-2, accesses Mar. 7, 2011.
Notice of Allowance mailed Apr. 1, 2011, in U.S. Appl. No. 12/642,506.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Dec. 8, 2010, in U.S. Appl. No. 12/642,473.
Notice of Allowance mailed in co-pending U.S. Appl. No. 12/339,753, dated Jul. 9, 2010.
Notice of Allowance mailed in co-pending U.S. Appl. No. 12/976,173, dated Aug. 29, 2011.
Notice of Allowance mailed in co-pending U.S. Appl. No. 12/642,468, dated Sep. 7, 2011.
Notice of Allowance mailed in co-pending U.S. Appl. No. 12/976,124, dated Oct. 24, 2011.
Notice of Allowance mailed in co-pending U.S. Appl. No. 12/976,150, dated Oct. 20, 2011.
Notice of Allowance mailed in co-pending U.S. Appl. No. 12/976,173, dated Nov. 14, 2011.
Notice of Allowance mailed Jan. 28, 2011, in U.S. Appl. No. 12/642,592.
Notice of Allowance mailed Jun. 11, 2010, in U.S. Appl. No. 12/642,489.
Notice of Allowance mailed Mar. 9, 2011, in U.S. Appl. No. 12/642,473.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Dec. 17, 2010, in co-pending U.S. Appl. No. 12/642,451.
Office Action mailed Feb. 1, 2010, in co-pending U.S. Appl. No. 12/339,753.
Office Action mailed Jun. 8, 2011, in co-pending U.S. Appl. No. 12/339,781.
Office Action mailed Mar. 15, 2010, in co-pending U.S. Appl. No. 12/339,820.
Office Action mailed Mar. 16, 2011, in co-pending U.S. Appl. No. 12/642,583.
Office Action mailed Mar. 29, 2011, in co-pending U.S. Appl. No. 12/642,468.
Office Action mailed Nov. 22, 2010, in co-pending U.S. Appl. No. 12/642,593.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.
STIC Search Report for U.S. Appl. No. 12/976,173.
Ullmann's Encyclopedia of Industrial Chemistry, "Hair Preparations," Wiley-VCH Verlag GnbH & Co., KGaA, Weinheim, p. 20 (2006).

* cited by examiner

AGENT FOR DYEING AND/OR BLEACHING KERATIN FIBERS, COMPRISING COMPOSITION (A), ANHYDROUS COMPOSITION (B), AND AT LEAST ONE FATTY SUBSTANCE

This application claims benefit of U.S. Provisional Application No. 61/294,929, filed Jan. 14, 2010. This application also claims benefit of priority under 35 U.S.C. §119 to French Patent Application No. 0959388, filed Dec. 22, 2009.

The present disclosure relates to an agent composed of two or more parts for dyeing and/or bleaching keratin fibers, for example, human keratin fibers such as the hair.

Among the methods for dyeing human keratin fibers, such as the hair, mention may be made of oxidation dyeing or permanent dyeing. For example, this dyeing method uses at least one oxidation dye precursor, usually at least one oxidation base optionally combined with at least one coupler.

In general, oxidation bases are chosen from ortho- or para-phenylenediamines, ortho- or para-aminophenols and heterocyclic compounds. These oxidation bases are colorless or weakly colored compounds, which, when combined with oxidizing products, can give access to colored species via a process of oxidative condensation.

The shades obtained with these oxidation bases are often varied by combining them with at least one coupler. The coupler can be chosen from aromatic meta-diamines, meta-aminophenols, meta-diphenols and certain heterocyclic compounds, such as indole compounds.

The variety of molecules used as oxidation bases and couplers allows a wide range of colours to be obtained.

Direct dyeing or semi-permanent dyeing is also known. The process conventionally used in direct dyeing consists of applying to the keratin fibers direct dyes, which are colored and coloring molecules that have affinity for the fibers, leaving them on for a time to allow the molecules to penetrate, by diffusion, into the fiber, and then rinsing them off.

The direct dyes generally used can be chosen from nitrobenzene, anthraquinone, nitropyridine, azo, methine, azomethine, xanthene, acridine, azine and triarylmethane direct dyes.

This type of process does not require the use of an oxidizing agent to develop the coloration. However, it is not excluded to use one in order to obtain, along with the coloration, a lightening effect. Such a process is referred to as direct dyeing or semi-permanent dyeing under lightening conditions.

Processes of permanent or semi-permanent dyeing under lightening conditions thus usually consist of using, along with the dye composition, an aqueous composition comprising at least one oxidizing agent, under alkaline pH conditions. The role of this oxidizing agent is to degrade the melanin of the hair, and, depending on the nature of the oxidizing agent, it can lead to more or less pronounced lightening of the fibers. Thus, for relatively weak lightening, the oxidizing agent is generally hydrogen peroxide. When more substantial lightening is desired, peroxygenated salts, for instance persulfates, are usually used in the presence of hydrogen peroxide.

In order to improve the performance of processes for dyeing and/or bleaching human keratin fibers, and to limit the inconveniences associated with the use of alkaline agents and oxidizing agents, it has been proposed to use in dye compositions a substantial amount of at least one fatty substance such as oils.

However, the incorporation into these compositions of a sufficient amount of oil can be problematic in terms of stability. Specifically, these compositions may be thermodynamically unstable, heat-sensitive and their viscosity changes over time. The problem can be more prominent when the oil content is increased.

There is a need to have satisfactory efficacy for lightening and dyeing products, for instance, in terms of lightening capacity or dyeing strength and/or selectivity, while at the same time reducing the harmful effects associated with the simultaneous presence of alkaline agents and oxidizing agents such as hydrogen peroxide, while reducing the degradation of the keratin fibers and reducing the inconveniences associated with the odor of the alkaline agents used, such as ammonia and amines.

It is thus sought to improve the effects of the alkaline agents and/or oxidizing agents while at the same time having maximum dyeing or lightening efficacy on keratin fibers.

This aim and others can be achieved by the present disclosure, one aspect of which is thus an agent for bleaching/dyeing the hair, comprising:

composition (A) comprising at least one basifying agent, and anhydrous composition (B) comprising hydrogen peroxide and/or at least one hydrogen peroxide precursor;

wherein composition (A) and/or composition (B) comprise at least one fatty substance not containing any carboxylic acid functional groups, such that the total amount of at least one fatty substance not containing any carboxylic acid functional groups in the agent after mixing the direct emulsion (A) and the inverse emulsion (B) being greater than 20% by weight.

The disclosure also relates to a process for treating human keratin fibers using this dyeing/bleaching agent.

Furthermore, the present disclosure relates to a multi-compartment device comprising, in at least one of the compartments, an composition (A) comprising at least one basifying agent, and, in the other, an anhydrous composition (B) comprising hydrogen peroxide or a hydrogen peroxide precursor, wherein composition (A) and/or composition (B) comprise at least one fatty substance not containing any carboxylic acid functional groups, and the total amount of fatty substances not containing any carboxylic acid functional groups is present in the mixture of composition (A) and composition (B) in an amount greater than 20% by weight.

When the agent according to the disclosure is intended for dyeing keratin fibers, composition (A) also comprises at least one oxidation dye and/or at least one direct dye.

Conversely, when the agent according to the disclosure is intended solely for bleaching keratin fibers, compositions (A) and (B) do not comprise any direct dyes or any oxidation dyes (bases and couplers) or, if they are present, their total content does not exceed 0.005% by weight relative to the weight of each composition. Accordingly, at such a content, only the composition would be dyed, i.e. no dyeing effect would be observed on the keratin fibers.

Compositions (A) and (B) of the dyeing and/or bleaching composition according to the disclosure are stable, and their viscosity changes little or not at all over time. It is thus easy to apply and shows very good efficacy, for instance in terms of quality and uniformity of dyeing and/or bleaching.

In addition, when it is intended for dyeing keratin fibers, the agent according to the disclosure can result in at least one of the benefits chosen from efficient uptake of the dyes onto the fibers, good power and chromaticity of the dyeing obtained, and also reduced dyeing selectivity along the same fiber or between fibers that are differently sensitized.

When it is intended for bleaching keratin fibers, the agent according to the disclosure can have lightening performance equivalent to or even greater than that obtained with the existing compositions, such as those based on ammonium hydroxide.

The agent according to the disclosure can also have the benefit of limiting the aggressive odours during its preparation or its application to the fibers.

Other characteristics and benefits of the disclosure will emerge more clearly on reading the description and the examples that follow.

In the text hereinbelow, and unless otherwise indicated, the limits of a range of values are included in that limit.

As used herein, the term "anhydrous composition" means a composition containing less than 5% by weight of water, for example, less than 1% by weight of water. For example, the anhydrous hydrogen peroxide and/or hydrogen peroxide precursor compositions can contain less than 5% by weight of water, for example, less than 1% by weight of water.

The human keratin fibers treated via the process according to the disclosure includes the hair.

According to the present disclosure, composition (A) comprises at least one basifying agent. This at least one basifying agent may be chosen from mineral or organic or hybrid basifying agents, or mixtures thereof.

The mineral basifying agents are, for example, chosen from aqueous ammonia, alkali metal carbonates or bicarbonates such as sodium or potassium carbonates or bicarbonates, sodium hydroxide and potassium hydroxide, and mixtures thereof.

The organic basifying agents can be chosen from, for example, organic amines whose pKb at 25° C. is less than 12, or less than 10, such as less than 6. The pKb corresponds to the function of highest basicity.

Hybrid compounds that may be mentioned include, but are not limited to, the salts of the amines mentioned previously with acids such as carbonic acid or hydrochloric acid.

The organic basifying agents can be chosen, for example, from alkanolamines, oxyethylenated ethylenediamines, oxypropylenated ethylenediamines, amino acids and the compounds of formula (I):

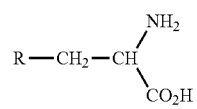

wherein W is a $C_1$-$C_6$ alkylene residue optionally substituted with a hydroxyl group or a $C_1$-$C_6$ alkyl radical; Rx, Ry, Rz and Rt, which may be identical or different, are chosen from a hydrogen atom, a $C_1$-$C_6$ alkyl, $C_1$-$C_6$ hydroxyalkyl and $C_1$-$C_6$ aminoalkyl radicals.

Examples of such amines that may be mentioned include, but are not limited to, 1,3-diaminopropane, 1,3-diamino-2-propanol, spermine and spermidine.

As used herein, the term "alkanolamine" means an organic amine comprising a primary, secondary or tertiary amine function, and at least one linear or branched $C_1$-$C_8$ alkyl groups bearing at least one hydroxyl radical.

Alkanolamines such as mono-, di- or tri-alkanolamines comprising from one to three identical or different $C_1$-$C_4$ hydroxyalkyl radicals are for example, suitable for performing the disclosure.

Non-limiting examples that may be mentioned include monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

For example, the amino acids that may be used are of natural or synthetic origin, in L, D or racemic form, and comprise at least one acid functional group chosen from, for example, carboxylic acid, sulfonic acid, phosphonic acid and phosphoric acid functional groups. The amino acids may be in their neutral or ionic form.

As amino acids that may be used in the present disclosure, non-limiting mention may be made for example of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

For example, the amino acids can include basic amino acids comprising an additional basic functional group optionally included in a ring or in a ureido function.

Such basic amino acids are, for example, chosen from those of formula (II):

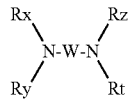

in which R denotes a group chosen from:

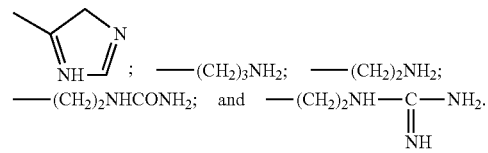

The compounds corresponding to formula (II) are histidine, lysine, arginine, ornithine and citrulline.

The organic amine may also be chosen from organic amines of heterocyclic type. Besides histidine that has already been mentioned in the amino acids, non-limiting mention may be made for example of pyridine, piperidine, imidazole, triazole, tetrazole and benzimidazole.

The organic amine may also be chosen from amino acid dipeptides. As amino acid dipeptides that may be used in the present disclosure, non-limiting mention may be made for example of carnosine, anserine and baleine.

The organic amine may also be chosen from compounds comprising a guanidine function. As amines of this type that may be used in the present disclosure, besides arginine that has already been mentioned as an amino acid, non-limiting mention may be made of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl] amino)ethane-1-sulfonic acid.

Non-limiting mention may be made for example of the use of guanidine carbonate or monoethanolamine hydrochloride as hybrid compounds.

The at least one basifying agent is, for example, chosen from aqueous ammonia, alkali metal carbonates, alkanolamines and derivatives thereof, sodium hydroxide, potassium hydroxide and the compounds of formula (I).

According to at least one embodiment, composition (A) contains at least one organic amine, for example, at least one alkanolamine as alkaline agents. When the composition contains several alkaline agents such as an alkanolamine, aqueous ammonia or a salt thereof, the organic amines can be in weight majority relative to the amount of ammonia.

According to at least one embodiment of the present disclosure, when composition (A) contains aqueous ammonia, it also contains at least one alkanolamine, and the weight amount of alkanolamine(s) in composition (A) is greater than the weight amount of ammonia in this same composition.

According to at least one embodiment of the present disclosure, composition (A) does not contain any aqueous ammonia.

Composition (A) can have a content of at least one basifying agent ranging from 0.1% to 40% by weight, for example, from 0.5% to 20% by weight relative to the weight of this composition.

Composition (A) can have a pH of greater than or equal to 8, for example, ranging from 8.5 to 11.5.

This pH may also be adjusted to the desired value by using, in addition to the at least one basifying agent, at least one acidifying agent.

Among the acidifying agents, non-limiting examples that may be mentioned include mineral or organic acids, for instance hydrochloric acid, orthophosphoric acid or sulfuric acid, carboxylic acids, for instance acetic acid, tartaric acid, citric acid or lactic acid, and sulfonic acids.

Composition (A) may comprise at least 25% by weight, for example, at least 30%, such as at least 35% by weight of fatty substances not containing any carboxylic acid functional groups.

In the present disclosure, the term "fatty substance" means an organic compound which is insoluble in water, at ordinary temperature (25° C.) and at atmospheric pressure (760 mmHg), i.e. which has a weight solubility in water of less than 5%, for example, less than 1%, such as less than 0.1%. The at least one fatty substance may have in their structure at least one sequence of at least two siloxane groups or a hydrocarbon-based chain comprising at least six carbon atoms. In addition, the at least one fatty substance is generally soluble in organic solvents under the same temperature and pressure conditions, for instance chloroform, ethanol, benzene, liquid petroleum jelly or decamethylcyclopentasiloxane.

In the context of the disclosure, the at least one fatty substance does not comprise any carboxylic acid functional groups. The term "fatty substance not containing any carboxylic acid functional groups" denotes a fatty substance not containing any —COOH groups or any —COO-groups.

According to the disclosure, the at least one fatty substance not containing any carboxylic acid functional groups is chosen from compounds that are liquid or pasty, for example, liquid, at room temperature and at atmospheric pressure.

The at least one fatty substance not containing any carboxylic acid functional groups can be for example, chosen from $C_6$-$C_{16}$ lower alkanes, non-silicone oils of mineral, plant, animal or synthetic origin, fatty alcohols, fatty acid esters, fatty alcohol esters, non-silicone waxes and silicones.

For the purposes of the disclosure, the fatty alcohols and fatty acids contain, for example, at least one linear or branched, saturated or unsaturated hydrocarbon-based group containing 6 to 30 carbon atoms, which are optionally substituted, for example with at least one hydroxyl group (such as from 1 to 4). If they are unsaturated, these compounds may comprise one to three conjugated or non-conjugated carbon-carbon double bonds.

In regard to the $C_6$-$C_{16}$ lower alkanes, they can be linear or branched, and possibly cyclic. Non-limiting examples that may be mentioned include hexane, dodecane and isoparaffins such as isohexadecane and isodecane.

As oils of mineral, plant, animal or synthetic origin that may be used in the present disclosure, non-limiting examples that may be mentioned include:

hydrocarbon-based oils of animal origin, such as perhydrosqualene;

triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;

linear or branched hydrocarbons of mineral or synthetic origin, containing more than 16 carbon atoms, such as liquid paraffins, petroleum jelly, liquid petroleum jelly, polydecenes and hydrogenated polyisobutenes such as PARLEAM®;

fluoro oils, for instance perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the disclosure may be chosen from, for example, branched or unsaturated alcohols containing from 8 to 30 carbon atoms. Non-limiting examples that may be mentioned include cetyl alcohol, cetearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

In regard to the esters of fatty acids and/or of fatty alcohols, they can be different from the triglycerides mentioned above; non-limiting mention may be made of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters, for example, being greater than or equal to 10.

Among the monoesters, non-limiting mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, and 2-hexyldecyl laurate.

In at least one embodiment, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

The following esters may also be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, non-limiting examples include ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ for example $C_{12}$-$C_{22}$ fatty acids. The term "sugar" means oxygen-bearing hydrocarbon-based compounds containing several alcohol functional groups, with or without aldehyde or ketone functional groups, and which contain at least 4 carbon atoms. These sugars may be monosaccharides, oligosaccharides or polysaccharides.

Non-limiting examples of suitable sugars that may be mentioned include sucrose (or saccharose), glucose, galactose, ribose, fructose, maltose, mannose, arabinose, xylose and lactose, and derivatives thereof, for example, alkyl derivatives, such as methyl derivatives, for instance methylglucose.

The sugar esters of fatty acids may be chosen, for example, from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or non-conjugated carbon-carbon double bonds.

In at least one embodiment, the esters may also be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, oleopalmitate, oleostearate and palmitostearate mixed esters.

The esters may also be chosen from monoesters and diesters and, for example, sucrose, glucose or methylglucose mono- or dioleates, stearates, behenates, oleopalmitates, linoleates, linolenates, and oleostearates.

An example that may be mentioned is the product sold under the name GLUCATE® DO by the company Amerchol, which is a methylglucose dioleate.

Non-limiting examples of esters or mixtures of esters of sugar and of fatty acid include:

the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name RYOTO SUGAR ESTERS, for example referenced B370 and corresponding to sucrose behenate formed from 20% monoester and 80% di-triester-polyester;

the sucrose monodipalmitostearate sold by the company Goldschmidt under the name TEGOSOFT® PSE.

The non-silicone wax(es) that may be used as fatty substances are chosen for example from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant sold by the company Bertin (France), animal waxes, for instance beeswaxes, or modified beeswaxes (cerabellina); other waxes or waxy raw materials that may be used according to the disclosure include for example, marine waxes such as the product sold by the company Sophim under the reference M82, and waxes of polyethylene or of polyolefins in general.

The silicones that may be used as fatty substances are volatile or non-volatile, cyclic, linear or branched silicones, which are unmodified or modified with organic groups, having a viscosity from $5 \times 10^{-6}$ to 2.5 m$^2$/s at 25° C., for example from $1 \times 10^{-5}$ to 1 m$^2$/s.

The silicones that may be used in accordance with the disclosure may be in the form of oils, waxes, resins or gums.

For example, the silicone is chosen from polydialkylsiloxanes, such as polydimethylsiloxanes (PDMS), and organomodified polysiloxanes comprising at least one functional group chosen from poly(oxyalkylene) groups, amino groups and alkoxy groups.

The organopolysiloxanes are defined in greater detail in Walter Noll's *Chemistry and Technology of Silicones* (1968) Academic Press. They can be volatile or non-volatile.

For example, when they are volatile, the silicones can be chosen from those having a boiling point ranging from 60° C. to 260° C., such as:

(i) cyclic polydialkylsiloxanes containing from 3 to 7 such as 4 to 5 silicon atoms. These are, for example, octamethylcyclotetrasiloxane sold, for example, under the name VOLATILE SILICONE® 7207 by Union Carbide, or SILBIONE® 70045 V2 by Rhodia, decamethylcyclopentasiloxane sold under the name VOLATILE SILICONE® 7158 by Union Carbide, or SILBIONE® 70045 V5 by Rhodia, and mixtures thereof.

Non-limiting mention may also be made of cyclocopolymers of the dimethylsiloxane/methylalkylsiloxane type, such as VOLATILE SILICONE® FZ 3109 sold by the company Union Carbide, of formula:

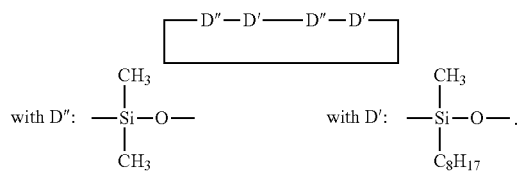

Non-limiting mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold, for example, under the name SH 200 by the company Toray Silicone. Silicones belonging to this category are also described in the article published in Cosmetics and Toiletries, Vol. 91, Jan. 76, pp. 27-32, Todd & Byers: *Volatile Silicone Fluids for Cosmetics*.

Non-volatile polydialkylsiloxanes, polydialkylsiloxane gums and resins, polyorganosiloxanes modified with organofunctional groups above, and mixtures thereof, can be used.

These silicones can be chosen from, for example polydialkylsiloxanes, among which non-limiting mention may be made mainly of polydimethylsiloxanes containing trimethylsilyl end groups. The viscosity of the silicones is measured, for example, at 25° C. according to ASTM standard 445 Appendix C.

Among these polydialkylsiloxanes, mention may be made, in a non-limiting manner, of the following commercial products:
 the SILBIONE® oils of the 47 and 70 047 series or the MIRASIL® oils sold by Rhodia, for instance the oil 70 047 V 500 000;
 the oils of the MIRASIL® series sold by the company Rhodia;
 the oils of the 200 series from the company Dow Corning, such as DC200 with a viscosity of 60,000 mm$^2$/s;
 the VISCASIL® oils from General Electric and certain oils of the SF series (SF 96, SF 18) from General Electric.

Non-limiting mention may also be made of polydimethylsiloxanes containing dimethylsilanol end groups known under the name DIMETHICONOL (CTFA), such as the oils of the 48 series from the company Rhodia.

In this category of polydialkylsiloxanes, non-limiting mention may also be made of the products sold under the names ABIL WAX® 9800 and 9801 by the company Goldschmidt, which are poly($C_1$-$C_{20}$)dialkylsiloxanes.

The silicone gums that can be used in accordance with the disclosure can be, for example, polydialkylsiloxanes, for example, polydimethylsiloxanes with high number-average molecular masses of ranging from 200,000 and 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used in accordance with the disclosure include mixtures such as:
 mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
 mixtures formed from a polydimethylsiloxane gum with a cyclic silicone, such as the product SF 1214 SILICONE FLUID from the company General Electric; this product is an SF 30 gum corresponding to a dimethicone, having a number-average molecular weight of 500,000, dissolved in the oil SF 1202 SILICONE FLUID corresponding to decamethylcyclopentasiloxane;
 mixtures of two PDMSs with different viscosities, for example, mixture of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6}$ m$^2$/s. This product may contain 15% SE 30 gum and 85% SF 96 oil.

The organopolysiloxane resins that can be used in accordance with the disclosure are crosslinked siloxane systems containing the following units:

$R_2SiO_{2/2}$, $R_3SiO_{1/2}$, $RSiO_{3/2}$ and $SiO_{4/2}$ in which R represents an alkyl containing 1 to 16 carbon atoms. For example, R can denote a $C_1$-$C_4$ lower alkyl radical, such as methyl.

Among these resins, non-limiting mention may be made of the product sold under the name Dow Corning 593 or those sold under the names Silicone Fluid SS 4230 and SS 4267 by the company General Electric, which are silicones of dimethyl/trimethylsiloxane structure.

Non-limiting mention may also be made of the trimethyl siloxysilicate type resins sold in particular under the names X22-4914, X21-5034 and X21-5037 by the company Shin-Etsu.

The organomodified silicones that can be used in accordance with the disclosure are silicones as defined above and comprising in their structure at least one organofunctional group attached via a hydrocarbon-based radical.

Besides the silicones described above, the organomodified silicones may include, for example, polydiarylsiloxanes, such as polydiphenylsiloxanes, and polyalkylarylsiloxanes functionalized with the organofunctional groups mentioned previously.

The polyalkylarylsiloxanes can be chosen from linear and/or branched polydimethyl/methylphenylsiloxanes and polydimethyl/diphenylsiloxanes with a viscosity of from $1 \times 10^{-5}$ to $5 \times 10^{-2}$ m$^2$/s at 25° C.

Among these polyalkylarylsiloxanes, non-limiting examples that may be mentioned include the products sold under the following names:
 the SILBIONE® oils of the 70 641 series from Rhodia;
 the oils of the RHODORSIL® 70 633 and 763 series from Rhodia;
 the oil DOW CORNING 556 COSMETIC GRADE FLUID from Dow Corning;
 the silicones of the PK series from Bayer, such as the product PK20;
 the silicones of the PN and PH series from Bayer, such as the products PN1000 and PH1000;
 certain oils of the SF series from General Electric, such as SF 1023, SF 1154, SF 1250 and SF 1265.

Among the organomodified silicones, non-limiting mention may be made of polyorganosiloxanes comprising:
 substituted or unsubstituted amine groups, such as the products sold under the name GP 4 SILICONE FLUID and GP 7100 by the company Genesee, or the products sold under the names Q2 8220 and DOW CORNING 929 or 939 by the company Dow Corning. The substituted amine groups are, for example, $C_1$-$C_4$ aminoalkyl groups;
 alkoxylated groups such as the product sold under the name Silicone Copolymer F-755 by SWS Silicones, and ABIL WAX® 2428, 2434 and 2440 by the company Goldschmidt.

For example, in at least one embodiment, the at least one fatty substance does not comprise any oxyalkylene units or any glycerol units.

In at least one embodiment of the disclosure, the at least one fatty substance is liquid at room temperature (25° C.) and at atmospheric pressure (760 mmHg).

The at least one fatty substance not containing any carboxylic acid functional groups can be, for example, chosen from $C_6$-$C_{16}$ lower alkanes, non-silicone oils of mineral, plant or synthetic origin, fatty alcohols, fatty acid esters, fatty alcohol esters and silicones.

In at least one embodiment, the at least one fatty substance of the composition according to the disclosure is non-silicone.

According to at least one embodiment, the at least one fatty substance is chosen from liquid paraffins, liquid petroleum jelly, polydecenes, liquid esters of fatty acids and/or of fatty alcohols, and mixtures thereof.

According to at least one embodiment, the at least one fatty substance is liquid petroleum jelly.

According to at least one embodiment, composition (A) that is useful in the present disclosure comprises at least one oxidation dye and/or one direct dye.

The oxidation dyes are generally chosen from oxidation bases and couplers.

By way of example, the oxidation bases can be chosen from para-phenylenediamines, bis(phenyl)alkylenediamines, para-aminophenols, ortho-aminophenols and heterocyclic bases, and the addition salts thereof.

Among the para-phenylenediamines, non-limiting examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, may further be mentioned.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present disclosure are, for example, the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-yl-pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 2526099; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5- diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole may also be used.

In at least one embodiment, 4,5-diaminopyrazole can be used, such as 4,5-diamino-1-(β-hydroxyethyl)pyrazole and/or a salt thereof.

Pyrazoles that may also be mentioned include, but are not limited to, diamino-N,N-dihydropyrazolopyrazolones, for example, those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylamino-pyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

For example, 2,3-diamino-6,7-dihydro-1H,5H-pyrazolo[1,2-a]pyrazol-1-one and/or a salt thereof can be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof can be used as heterocyclic bases.

Among the couplers that may be used, non-limiting mention may be made for example of meta-phenylenediamines, meta-aminophenols, meta-diphenols, naphthalene-based couplers and heterocyclic couplers, and also the addition salts thereof.

Non-limiting mention may be made, for example, of 1,3-dihydroxybenzene, 1,3-dihydroxy-2-methylbenzene, 4-chloro-1,3-dihydroxybenzene, 2,4-diamino-1-(3-hydroxyethyloxy)benzene, 2-amino-4-(3-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

The addition salts of the oxidation bases and couplers are chosen from the addition salts with an acid such as the hydrochlorides, hydrobromides, sulfates, citrates, succinates, tartrates, lactates, tosylates, benzenesulfonates, phosphates and acetates.

The at least one oxidation base can each be present in an amount ranging from 0.0001% to 10% by weight relative to the total weight of the composition, for example, from 0.005% to 5% by weight relative to the total weight of the composition.

The content of the at least one coupler, if present, each represents from 0.0001% to 10% by weight relative to the total weight of the composition, for example, from 0.005% to 5% by weight relative to the total weight of the composition.

The direct dyes that may be used are, for example, synthetic or natural dyes, chosen from ionic or nonionic species, preferably cationic or nonionic species.

Non-limiting examples of suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and for example anthraquinone, naphthoquinone or benzoquinone direct dyes; azine; xanthene; triarylmethane; indoamine; indigoid; phthalocyanins, porphyrins and natural direct dyes, alone or as mixtures. For example, non-limiting mention may be made of direct dyes from among: azo; methine; carbonyl; azine; nitro (hetero) aryl; tri(hetero)arylmethane; porphyrin; phthalocyanin, and natural direct dyes, alone or as mixtures.

Among the benzenic direct dyes that may be used according to the disclosure, non-limiting mention may be made in a non-limiting manner of the following compounds:

1,4-diamino-2-nitrobenzene,
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene 1-hydroxy-6-bis(β-hydroxyethyl)amino-3-nitrobenzene 1-β-hydroxyethylamino-2-nitrobenzene 1-hydroxy-4-β-hydroxyethylamino-3-nitrobenzene.

Among the azo, azomethine, methine and tetraazapentamethine direct dyes that may be used according to the disclosure, non-limiting mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

Thus, non-limiting mention may be made for example of the following dyes of formulae (I) to (IV), such as the compounds of formulae (III), (IV), (V) and (V'):

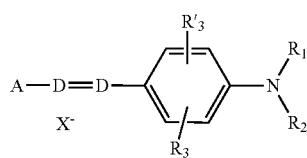
(III)

wherein,

D represents a nitrogen atom or a —CH group, for example a nitrogen atom, $R_1$ and $R_2$, which may be identical or different, represent a hydrogen atom; a $C_1$-$C_4$ alkyl radical which may be substituted with a —CN, —OH or —NH$_2$ radical, or form, with a carbon atom of the benzene ring, a heterocycle optionally containing oxygen or nitrogen, which may be substituted with at least one $C_1$-$C_4$ alkyl radical; a 4'-aminophenyl radical, $R_3$ and $R'_3$, which may be identical or different, represent a hydrogen atom or a halogen atom chosen from chlorine, bromine, iodine and fluorine, or a cyano, $C_1$-$C_4$ alkyl, $C_1$-$C_4$ alkoxy or acetyloxy radical, X⁻ represents an anion for example chosen from chloride, methyl sulfate and acetate, A represents a group chosen from structures A1 to A18, and for example chosen from A1, A4, A7, A13 and A18, below:

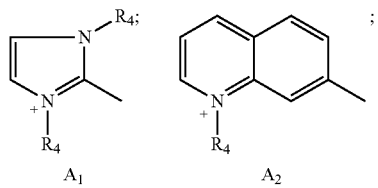

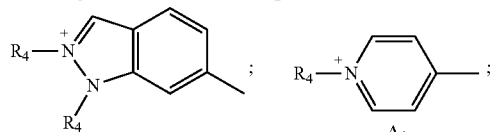

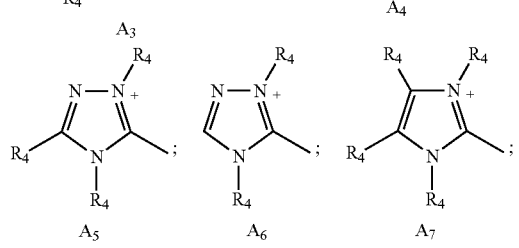

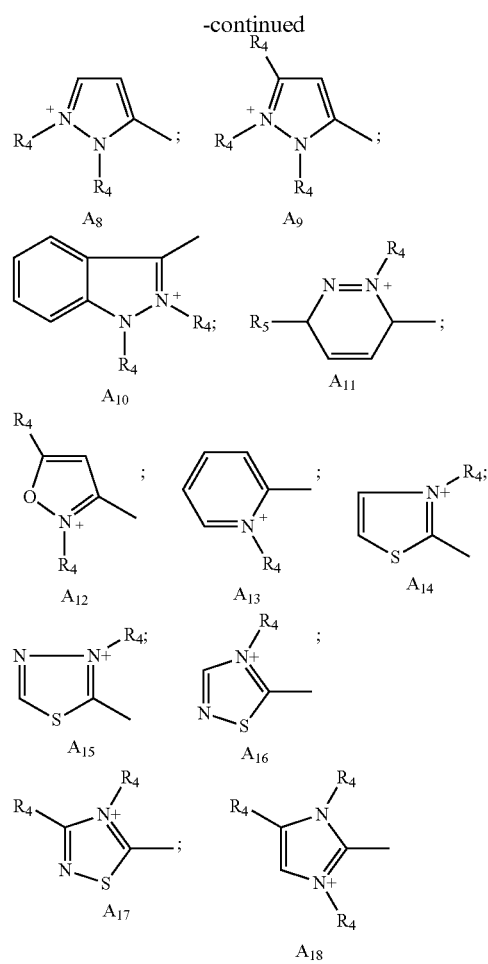

wherein $R_4$ represents a $C_1$-$C_4$ alkyl radical which may be substituted with a hydroxyl radical and $R_5$ represents a $C_1$-$C_4$ alkoxy radical;

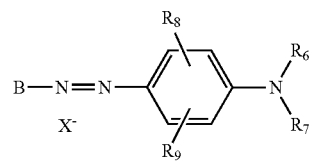
(IV)

wherein, $R_6$ represents a hydrogen atom or a $C_1$-$C_4$ alkyl radical, $R_7$ represents a hydrogen atom, an alkyl radical which may be substituted with a —CN radical or with an amino group, a 4'-aminophenyl radical, or forms with $R_6$ a heterocycle optionally containing oxygen and/or nitrogen, which may be substituted with a $C_1$-$C_4$ alkyl radical, $R_8$ and $R_9$, which may be identical or different, represent a hydrogen atom, a halogen atom such as bromine, chlorine, iodine or fluorine, a $C_1$-$C_4$ alkyl or $C_1$-$C_4$ alkoxy radical, or a —CN radical, X⁻ represents an anion for example chosen from chloride, methyl sulfate and acetate, B represents a group chosen from structures B1 to B6 below:

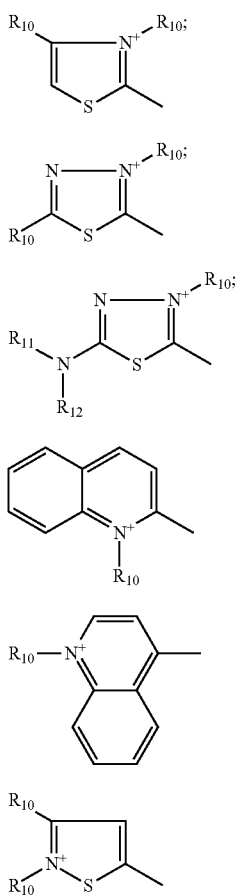

B1
B2
B3
B4
B5
B6 wherein $R_{10}$ represents a $C_1$-$C_4$ alkyl radical, $R_{11}$ and $R_{12}$, which may be identical or different, represent a hydrogen atom or a $C_1$-$C_4$ alkyl radical;

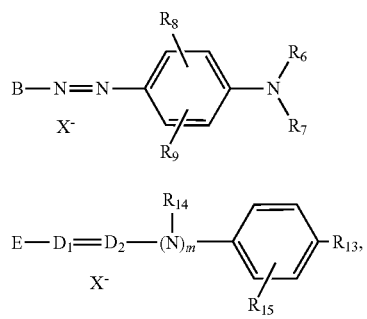

(V)
(V')

wherein,
$R_{13}$ represents a hydrogen atom, a $C_1$-$C_4$ alkoxy radical, a halogen atom such as bromine, chlorine, iodine or fluorine, or an amino radical,
$R_{14}$ represents a hydrogen atom, a $C_1$-$C_4$ alkyl radical or forms, with a carbon atom of the benzene ring, a heterocycle optionally containing oxygen and/or substituted with at least one $C_1$-$C_4$ alkyl group,
$R_{15}$ represents a hydrogen atom or a halogen atom such as bromine, chlorine, iodine or fluorine,
$R_{16}$ and $R_{17}$, which may be identical or different, represent a hydrogen atom or a $C_1$-$C_4$ alkyl radical,
$D_1$ and $D_2$, which may be identical or different, represent a hydrogen atom or a —CH group,
m=0 or 1,
with the understanding that when $R_{13}$ represents an unsubstituted amino group, then $D_1$ and $D_2$ simultaneously represent a —CH group and m=0,
$X^-$ represents an anion for example chosen from chloride, methyl sulfate and acetate, E represents a group chosen from structures E1 to E8, for example chosen from E1, E2 and E7, below:

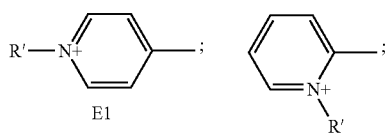

E1
E2

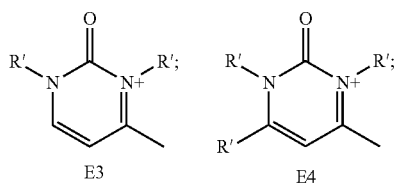

E3
E4

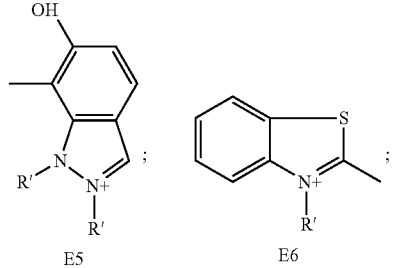

E5
E6

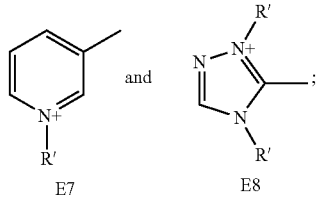

E7
E8 wherein R' represents a $C_1$-$C_4$ alkyl radical;
provided that,
when m=0 and $D_1$ represents a nitrogen atom, then E may also denote a group of structure E9 below:

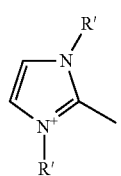

E9 wherein R' represents a $C_1$-$C_4$ alkyl radical.

G—N═N—J (VI)

wherein,

G represents a group chosen from the structures $G_1$, $G_2$ and $G_3$ below:

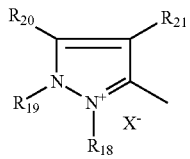

G₁

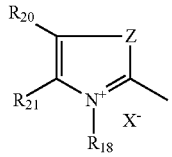

G₂

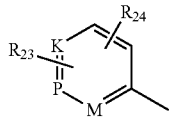

G₃ wherein, $R_{18}$ denotes a $C_1$-$C_4$ alkyl radical, a phenyl radical which may be substituted with a $C_1$-$C_4$ alkyl radical, or a halogen atom chosen from chlorine, bromine, iodine and fluorine;

$R_{19}$ denotes a $C_1$-$C_4$ alkyl radical or a phenyl radical;

$R_{20}$ and $R_{21}$, which may be identical or different, represent a $C_1$-$C_4$ alkyl radical, a phenyl radical, or form together in $G_1$ a benzene ring substituted with at least one $C_1$-$C_4$ alkyl, $C_1$-$C_4$ alkoxy or $NO_2$ radicals, or form together in $G_2$ a benzene ring optionally substituted with at least one $C_1$-$C_4$ alkyl, $C_1$-$C_4$ alkoxy or $NO_2$ radicals; $R_{20}$ may also denote a hydrogen atom;

Z represents an oxygen or sulfur atom or a group $-NR_{19}$;

M represents a group $-CH$, $-CR$ (R denoting $C_1$-$C_4$ alkyl) or $-NR_{22}(X^-)_r$;

K represents a group $-CH$, $-CR$ (R denoting $C_1$-$C_4$ alkyl) or $-NR_{22}(X^-)_r$;

P represents a group $-CH$, $-CR$ (R denoting $C_1$-$C_4$ alkyl) or $-NR_{22}(X^-)_r$;

r denotes 0 or 1;

$R_{22}$ represents an $O^-$ atom, a $C_1$-$C_4$ alkoxy radical or a $C_1$-$C_4$ alkyl radical;

$R_{23}$ and $R_{24}$, which may be identical or different, represent a hydrogen atom or a halogen atom chosen from chlorine, bromine, iodine and fluorine, a $C_1$-$C_4$ alkyl or $C_1$-$C_4$ alkoxy radical, or an $-NO_2$ radical;

$X^-$ represents an anion for example chosen from chloride, iodide, methyl sulfate, ethyl sulfate, acetate and perchlorate;

provided that, if $R_{22}$ denotes $O^-$, then r denotes zero;

if K or P or M denote $-N-(C_1$-$C_4)$alkyl $X^-$, then $R_{23}$ or $R_{24}$ is other than a hydrogen atom;

if K denotes $-NR_{22}(X^-)_r$, then $M=P=-CH$, $-CR$;

if M denotes $-NR_{22}(X^-)_r$, then $K=P=-CH$, $-CR$;

if P denotes $-NR_{22}(X^-)_r$, then K=M and denotes $-CH$ or $-CR$;

if Z denotes a sulfur atom with $R_{21}$ denoting $C_1$-$C_4$ alkyl, then $R_{20}$ is other than a hydrogen atom;

if Z denotes $-NR_{22}$ with $R_{19}$ denoting $C_1$-$C_4$ alkyl, then at least one of the radicals $R_{18}$, $R_{20}$ or $R_{21}$ of the group of structure $G_2$ is other than a $C_1$-$C_4$ alkyl radical;

J represents:

(a) a group of structure $J_1$ below:

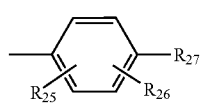

J₁ wherein structure $J_1$:

$R_{25}$ represents a hydrogen atom, a halogen atom chosen from chlorine, bromine, iodine and fluorine, a $C_1$-$C_4$ alkyl or $C_1$-$C_4$ alkoxy radical, an $-OH$, $-NO_2$, $-NHR_{28}$, $-NR_{29}R_{30}$ or $C_1$-$C_4$-NHCOalkyl radical, or forms with $R_{26}$ a 5- or 6-membered ring optionally containing at least one heteroatom chosen from nitrogen, oxygen and sulfur;

$R_{26}$ represents a hydrogen atom, a halogen atom chosen from chlorine, bromine, iodine and fluorine, a $C_1$-$C_4$ alkyl or $C_1$-$C_4$ alkoxy radical, or forms with $R_{27}$ or $R_{28}$ a 5- or 6-membered ring optionally containing at least one heteroatom chosen from nitrogen, oxygen and sulfur;

$R_{27}$ represents a hydrogen atom, an $-OH$ radical, a radical $-NHR_{28}$ or a radical $-NR_{29}R_{30}$;

$R_{28}$ represents a hydrogen atom, a $C_1$-$C_4$ alkyl radical, a $C_1$-$C_4$ monohydroxyalkyl, $C_2$-$C_4$ polyhydroxyalkyl radical or a phenyl radical;

$R_{29}$ and $R_{30}$, which may be identical or different, represent a $C_1$-$C_4$ alkyl radical, a $C_1$-$C_4$ monohydroxyalkyl or $C_2$-$C_4$ polyhydroxyalkyl radical;

(b) a 5- or 6-membered nitrogenous heterocyclic group, which may contain other heteroatoms and/or carbonyl groups and may be substituted with at least one $C_1$-$C_4$ alkyl, amino or phenyl radical, and for example a group of structure $J_2$ below:

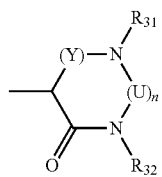

J₂ wherein, $R_{31}$ and $R_{32}$, which may be identical or different, represent a hydrogen atom, a $C_1$-$C_4$ alkyl radical or a phenyl radical;

Y denotes a $-CO-$ radical or a

radical;

n=0 or 1, with, when n denotes 1, U denotes a $-CO-$ radical.

In structures (III) to (VI) defined above, the $C_1$-$C_4$ alkyl or alkoxy group can denote, for example methyl, ethyl, butyl, methoxy or ethoxy.

Among the compounds of formulae (III) and (V), the following compounds may be used:

Among the azo direct dyes that may also be mentioned are the following dyes, described in the Color Index International, 3rd edition:

Disperse Red 17
Basic Red 22
Basic Red 76
Basic Yellow 57
Basic Brown 16
Basic Brown 17
Disperse Black 9.

Non-limiting mention may also be made of 1-(4'-aminodiphenylazo)-2-methyl-4-bis(β-hydroxyethyl)aminobenzene.

Among the quinone direct dyes that may be mentioned are the following dyes:

Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99 and also the following compounds:

1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes that may be mentioned are the following compounds:

Basic Blue 17
Basic Red 2.

Among the triarylmethane dyes that may be used according to the disclosure, non-limiting mention may be made of the following compounds:

Basic Green 1
Basic Violet 3
Basic Violet 14
Basic Blue 7
Basic Blue 26.

Among the indoamine dyes that may be used according to the disclosure, non-limiting mention may be made of the following compounds:

2-β-hydroxyethylamino-5-[bis(β-4'-hydroxyethyl)amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethyl,carbamylmethyl)amino]phenylureido-6-methyl-1,4-benzoquinone imine.

Among the dyes of tetraazapentamethine type that may be used according to the disclosure, non-limiting mention may be made of the following compounds given in the table below:

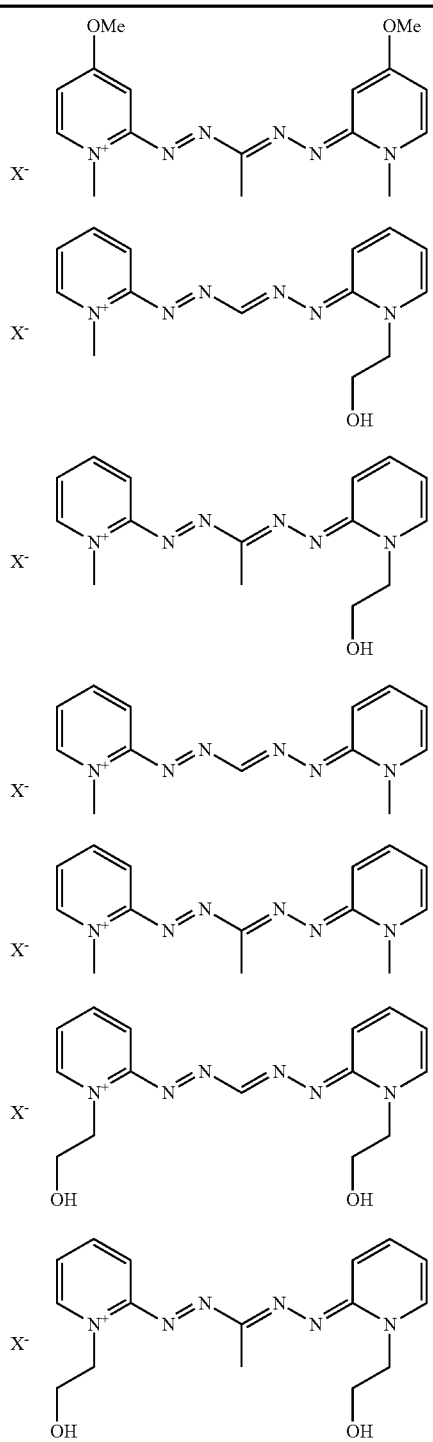

wherein X⁻ represents an anion for example chosen from chloride, iodide, methyl sulfate, ethyl sulfate, acetate and perchlorate.

Among the natural direct dyes that may be used according to the disclosure, non-limiting mention may be made of lawsone, juglone, alizarin, purpurin, carminic acid, kermesic acid, purpurogallin, protocatechaldehyde, indigo, isatin, curcumin, spinulosin, apigenidin, haematoxylin, haematin, brasilin, brasilein and orceins. It is also possible to use extracts or decoctions containing these natural dyes and for example henna-based poultices or extracts.

The direct dyes may be monochromophoric dyes (i.e. comprising only one dye) or polychromophoric, for example di- or trichromophoric; the chromophores possibly being identical or different, and from the same or different chemical families. It should be noted that a polychromophoric dye comprises several radicals each derived from a molecule that absorbs in the visible region ranging from 400 to 800 nm. Furthermore, this absorbance of the dye does not require any prior oxidation thereof, or combination with any other chemical species.

In the case of polychromophoric dyes, the chromophores are connected together via at least one linker, which may be cationic or non-cationic.

The linker can be a linear, branched or cyclic $C_1$-$C_{20}$ alkyl chain, optionally interrupted with at least one heteroatom (such as nitrogen or oxygen) and/or with at least one group comprising such an atom ($CO$, $SO_2$), optionally interrupted with at least one heterocycle that may or may not be fused to a phenyl nucleus and comprising at least one quaternized nitrogen atom engaged in the ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso or peroxy groups.

If the heterocycles or aromatic nuclei (phenyl or naphthyl) are substituted, they are substituted, for example, with at least one $C_1$-$C_8$ alkyl radical optionally substituted with a hydroxyl, $C_1$-$C_2$ alkoxy, $C_2$-$C_4$ hydroxyalkoxy, acetylamino, or amino group substituted with one or two $C_1$-$C_4$ alkyl radicals, optionally bearing at least one hydroxyl group, or the two radicals possibly forming, with the nitrogen atom to which they are attached, a 5- or 6-membered heterocycle optionally comprising another heteroatom identical to or different than nitrogen; a halogen atom; a hydroxyl group; a $C_1$-$C_2$ alkoxy radical; a $C_2$-$C_4$ hydroxyalkoxy radical; an amino radical; or an amino radical substituted with one or two identical or different $C_1$-$C_4$ alkyl radicals optionally bearing at least one hydroxyl group.

Among the polychromophoric dyes, mention may be made for example of symmetrical or non-symmetrical azo and/or azomethine (hydrazone) di- or trichromophoric dyes comprising, on the one hand, at least one optionally fused 5- or 6-membered aromatic heterocycle, comprising at least one quaternized nitrogen atom engaged in the said heterocycle and optionally at least one other heteroatom (such as nitrogen, sulfur or oxygen), and, on the other hand, at least one optionally substituted phenyl or naphthyl group, optionally bearing at least one group OR with R representing a hydrogen atom, an optionally substituted $C_1$-$C_6$ alkyl radical, an optionally substituted phenyl nucleus, or at least one group $N(R')_2$ with R', which may be identical or different, representing a hydrogen atom, an optionally substituted $C_1$-$C_6$ alkyl radical or an optionally substituted phenyl nucleus; the radicals R' possibly forming, with the nitrogen atom to which they are attached, a saturated 5- or 6-membered heterocycle, or alternatively one and/or both the radicals R' may each form, with the carbon atom of the aromatic ring located ortho to the nitrogen atom, or a saturated 5- or 6-membered heterocycle.

Aromatic cationic heterocycles that may be mentioned include 5- or 6-membered rings containing 1 to 3 nitrogen atoms for example 1 or 2 nitrogen atoms, one being quaternized; the heterocycle can be optionally fused to a benzene nucleus. It should similarly be noted that the heterocycle may optionally comprise another heteroatom other than nitrogen, for instance sulfur or oxygen.

The bonding between the linker, as defined previously, and each chromophore generally takes place via a heteroatom substituent on the phenyl or naphthyl nucleus or via the quaternized nitrogen atom of the cationic heterocycle.

The dye may comprise identical or different chromophores.

As examples of such dyes, reference may be made for example to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

It is also possible to use the cationic direct dyes mentioned in patent applications: EP 1 006 153, which describes dyes comprising two chromophores of anthraquinone type connected via a linker of cationic type; EP 1 433 472, EP 1 433 474, EP 1 433 471 and EP 1 433 473, which describe identical or different dichromophoric dyes, connected via a cationic or non-cationic linker, and also EP 6 291 333, which describes dyes, for example comprising three chromophores, one of them being an anthraquinone chromophore, to which are attached two chromophores of azo or diazacarbocyanin type or an isomer thereof.

When they are present, the direct dye(s) can represent from 0.0001% to 10% by weight, for example, from 0.005% to 5% by weight relative to the total weight of the composition.

Composition (A) may contain at least one surfactant. The surfactants that are useful may be anionic, cationic, amphoteric or nonionic.

The at least one surfactant that may be used can be chosen from nonionic surfactants and anionic surfactants, for example, from nonionic surfactants.

The anionic surfactants can be chosen from the salts (for example alkali metal salts, such as sodium salts, ammonium salts, amino salts such as amino alcohol salts or alkaline-earth metal salts such as magnesium salts) of the following compounds:
- alkyl sulfates, alkyl ether sulfates, alkylamido ether sulfates, alkylaryl polyether sulfates, monoglyceride sulfates;
- alkylsulfonates, alkylamidesulfonates, alkylarylsulfonates, α-olefin sulfonates, paraffin sulfonates;
- alkyl phosphates, alkyl ether phosphates;
- alkylsulfosuccinates, alkyl ether sulfosuccinates, alkylamidesulfosuccinates; alkylsulfosuccinates;
- alkylsulfoacetates;
- acylsarcosinates; acylisethionates and N-acyltaurates;
- salts of fatty acids such as oleic acid, ricinoleic acid, palmitic acid or stearic acid, coconut oil acid or hydrogenated coconut oil acid;
- alkyl-D-galactoside uronic acid salts;
- acyllactylates;
- salts of polyoxyalkylenated alkyl ether carboxylic acids, of polyoxyalkylenated alkylaryl ether carboxylic acids or of polyoxyalkylenated alkylamido ether carboxylic acids, for example, those containing from 2 to 50 ethylene oxide groups;
- and mixtures thereof.

The alkyl or acyl radical of these various compounds can contain from 6 to 24 carbon atoms, for example, from 8 to 24 carbon atoms, and the aryl radical can denote a phenyl or benzyl group.

The nonionic surfactants can be chosen from monooxyalkylenated or polyoxyalkylenated, monoglycerolated or polyglycerolated nonionic surfactants. The oxyalkylene units can be oxyethylene or oxypropylene units, or a combination thereof, for example, oxyethylene units.

Non-limiting examples of oxyalkylenated nonionic surfactants that may be mentioned include:
- oxyalkylenated ($C_8$-$C_{24}$)alkylphenols,
- saturated or unsaturated, linear or branched, oxyalkylenated $C_8$-$C_{30}$ alcohols,
- saturated or unsaturated, linear or branched, oxyalkylenated $C_8$-$C_{30}$ amides,
- esters of saturated or unsaturated, linear or branched, $C_8$-$C_{30}$ acids and of polyethylene glycols,
- polyoxyethylenated esters of saturated or unsaturated, linear or branched, $C_8$-$C_{30}$ acids and of sorbitol,
- saturated or unsaturated, oxyethylenated plant oils,
- condensates of ethylene oxide and/or of propylene oxide,
- and mixtures thereof.

These surfactants contain a number of moles of ethylene oxide and/or of propylene oxide ranging from 1 to 100, for example, from 2 to 50. For example, the nonionic surfactants do not comprise any oxypropylene units.

In accordance with at least one embodiment of the disclosure, the oxyalkylenated nonionic surfactants are chosen from oxyethylenated $C_8$-$C_{30}$ alcohols, and esters of $C_8$-$C_{30}$ acids and of polyethylene glycols.

As examples of monoglycerolated or polyglycerolated nonionic surfactants, monoglycerolated or polyglycerolated $C_8$-$C_{40}$ alcohols can be used.

For example, the monoglycerolated or polyglycerolated $C_8$-$C_{40}$ alcohols correspond to the following formula:

$$RO-[CH_2-CH(CH_2OH)-O]_m-H$$

wherein R represents a linear or branched $C_8$-$C_{40}$ and for example $C_8$-$C_{30}$ alkyl or alkenyl radical, and m represents a number ranging from 1 to 30 and for example from 1 to 10.

As examples of compounds that are suitable in the context of the disclosure, non-limiting mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

The monoglycerolated or polyglycerolated alcohols can be, for example, the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

According to at least one embodiment of the present disclosure, composition (A) comprises at least one nonionic surfactant.

In at least one embodiment, composition (A) contains at least one nonionic surfactant with an HLB of greater than or equal to 8.

When present, the at least one surfactant represents an amount ranging from 1% to 20% by weight, for example, ranging from 1% to 15% by weight, such as ranging from 2% to 10% by total weight of surfactant relative to the total weight of composition (A).

Composition (A) that is useful in the disclosure may comprise at least one fumed silica.

Fumed silicas may be obtained by high-temperature hydrolysis of a volatile silicon compound in an oxhydric flame, producing a finely divided silica. This process makes it possible to obtain, for example, hydrophilic silicas having a large number of silanol groups at their surface. Such hydrophilic silicas are sold, for example, under the names AEROSIL 130®, AEROSIL 200®, AEROSIL 255®, AEROSIL 300® and AEROSIL 380® by the company Degussa, and CAB-O-SIL HS-5®, CAB-O-SIL EH-5®, CAB-O-SIL LM-130®, CAB-O-SIL MS-55® and CAB-O-SIL M-5® by the company Cabot.

It is possible to chemically modify the surface of the silica by chemical reaction in order to reduce the number of silanol groups. Silanol groups may be substituted with hydrophobic groups to obtain a hydrophobic silica.

The hydrophobic groups may be:
   trimethylsiloxyl groups, which are obtained for example by treating fumed silica in the presence of hexamethyldisilazane. Silicas thus treated are known as "Silica silylate" according to the CTFA (6th edition, 1995). They are sold, for example, under the references AEROSIL R812® by the company Degussa and CAB-O-SIL TS-530® by the company Cabot.
   dimethylsilyloxyl or polydimethylsiloxane groups, which are obtained, for example by treating fumed silica in the presence of polydimethylsiloxane or dimethyldichlorosilane. Silicas thus treated are known as "Silica dimethyl silylate" according to the CTFA (6th edition, 1995). They are sold, for example, under the references AEROSIL R972® and AEROSIL R974® by the company Degussa, and CAB-O-SIL TS-610® and CAB-O-SIL TS-720® by the company Cabot.

The fumed silica can have a particle size that may be nanometric to micrometric, for example ranging from 5 to 200 nanometers.

When it is present, the fumed silica represents from 1% to 30% by weight relative to the weight of the composition.

Composition (A) in the present disclosure may also comprise at least one thickener.

The at least one thickener may be chosen from fatty acid amides such as coconut acid diethanolamide or monoethanolamide, oxyethylenated alkyl ether carboxylic acid monoethanolamide, polymeric thickeners such as cellulose-based thickeners such as hydroxyethylcellulose, hydroxypropylcellulose, carboxymethylcellulose, guar gum and derivatives thereof such as hydroxypropylguar, and clays, for example, bentonites and hectorites, and derivatives thereof.

The content of thickener(s), if they are present, usually ranges from 0.01%, to 20% by weight, for example, from 0.1% to 5% by weight relative to the weight of composition (A).

Composition (A) comprises water and optionally at least one organic solvent.

Non-limiting examples of organic solvents that may be mentioned include linear or branched and for example saturated monoalcohols, comprising 2 to 6 carbon atoms, such as ethanol or isopropanol; aromatic alcohols such as benzyl alcohol or phenylethyl alcohol; polyols containing more than two hydroxyl functional groups, such as glycerol; polyol ethers, for instance ethylene glycol monomethyl, monoethyl or monobutyl ether, propylene glycol or ethers thereof, for instance propylene glycol monomethyl ether; and also diethylene glycol alkyl ethers, for example $C_1$-$C_4$ alkyl ethers, for instance diethylene glycol monoethyl ether or monobutyl ether, alone or as a mixture.

The at least one organic solvent, when present, can be present in an amount ranging from 1% to 40% by weight relative to the total weight of each of the compositions, for example, from 5% to 30% by weight relative to the total weight of composition (A).

The amount of water in composition (A) may range from 5% to 90%, for example, from 10% to 80% by weight of water.

In at least one embodiment, the aqueous phase of composition (A) comprising water and the compounds that are soluble in water at room temperature (25° C.) and at atmospheric pressure (760 mmHg), for example, can be present in an amount ranging from 10% to 85% by weight of composition (A).

Composition (A) may be in various forms, such as in the form of liquids, milks or creams, or in any other form that is suitable for bleaching and/or dyeing keratin fibers, such as human hair. For example, in at least one embodiment it is in the form of a milk or a cream.

Composition (A) may be a direct emulsion or an inverse emulsion. For example, in at least one embodiment, composition (A) is a direct emulsion.

Composition (B) is an anhydrous composition containing hydrogen peroxide and/or at least one hydrogen peroxide precursor.

As hydrogen peroxide precursors that are useful in the present disclosure, non-limiting mention may be made of polymeric complexes that can release hydrogen peroxide, such as polyvinylpyrrolidone/$H_2O_2$, for example, in the form of powders, and the other polymeric complexes described in U.S. Pat. Nos. 5,008,093, 3,376,110 and 5,183,901. Non-limiting mention may also be made of urea peroxide and alkali metal, alkaline-earth metal or ammonium perborates and percarbonates.

It may be noted that alkali metal, alkaline-earth metal or ammonium persulfates are not included in these precursors since, in the redox mechanisms using these persulfates, there is no release of hydrogen peroxide.

The anhydrous hydrogen peroxide compositions that may be used in the present disclosure are known in the art. For example, document GB-A-632 084 describes antiseptic urea peroxide liquid solutions resulting from the combination of hydrogen peroxide and urea in a polyhydric alcohol; document DE-A-1 262 982 describes solutions of hydrogen peroxide in unsaturated dicarboxylic acid diesters or polyesters; document FR-A-2 145 400 describes solutions of a peroxide compound such as hydrogen peroxide in alkyl esters or in organic acids; document EP-121 660 describes a process for preparing solutions of hydrogen peroxide in various organic solvents that may be used for oxidation or epoxidation reactions. Document EP 193 471 describes an anhydrous hydrogen peroxide composition in an organic solvent that may be used for a cosmetic application. For example, the compositions described in that document, which contain hydrogen peroxide and at least one organic solvent.

The anhydrous hydrogen peroxide and/or hydrogen peroxide precursor compositions can contain less than 5% by weight of water, for example, less than 1% by weight of water.

Composition (B) may be in the form of a powder, in the form of a paste or a cream, or in the form of a thickened or unthickened liquid.

For example, the powder form can be used for the at least one hydrogen peroxide precursor. These powder forms may optionally be compacted.

In the powder forms, the oxidizing agent may represent from 5% to 100% by weight of composition (B). The optional pulverulent adjuvants present in these powder forms may or may not be water-soluble. Among the water-soluble pulverulent adjuvants that may be used, mention can be made of polysaccharides such as glucose, lactose, sucrose and sorbitol. Among the pulverulent adjuvants are also solid acidifying or basifying agents. Among the water-insoluble pulverulent adjuvants that may be mentioned are the silicas mentioned above, clays, polymers such as polyamides, TEFLON, polyalkyl methacrylates and glass beads.

In at least one embodiment of the disclosure, composition (B) consists of a dispersion or solution of hydrogen peroxide and/or of hydrogen peroxide precursors in a solvent or a mixture of solvents.

This or these organic solvents may be of very varied nature, for example:
1) fatty substances not containing any carboxylic acid functional groups, such as those mentioned previously,
2) alcohols that are at least partially water-soluble (for example with a solubility of greater than or equal to 4% in water at room temperature (25° C.) and atmospheric pressure (760 mmHg) such as ethanol, n-propanol, isopropanol or benzyl alcohol,
3) acyclic polyols such as glycols and for example propylene glycol, diethylene glycol, dipropylene glycol, tripropylene glycol or glycerol, and ethers thereof, such as propylene glycol monomethyl ether, diethylene glycol monoethyl ether or propylene glycol monoethyl ether, and
4) oligomeric polyethers such as those of ethylene oxide, of propylene oxide and ethers thereof, and also oligomeric polyethers corresponding to formula (VII) below:

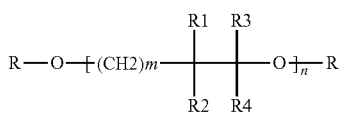

(VII)

wherein,

R represents a linear or branched alkyl radical containing from 1 to 12 carbon atoms, R1, R2, R3 and R4, which may be identical or different, are chosen from a hydrogen atom and an alkyl radical containing from 1 to 6 carbon atoms, wherein at least two of the radicals R1, R2, R3 or R4 represent a hydrogen atom, m is 1 to 4, and n is a mean value greater than or equal to 2, for example, ranging from 4 to 50, the number of carbon atoms in each repeating unit, which may be identical or different, being at least equal to 4.

The number-average molecular mass of these oligomeric polyethers can range from 200 to 5000 and their viscosity can range from 0.002 to 1 Pa·s, for example, from 0.01 to 0.1 Pa·s measured at 25° C.

Some of these oligomers are water-soluble, while others are not.

Among the oligomeric polyethers represented by the above formula, for example, polytetrahydrofuran dimethyl ether corresponding to formula (VIII):

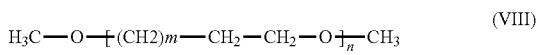

(VIII)

wherein n is a mean value ranging from 4 to 10.

The organic solvent must be stable in the presence of hydrogen peroxide and/or of the hydrogen peroxide precursor(s) under the conditions of use of anhydrous composition (B).

The processes for preparing the anhydrous hydrogen peroxide compositions are known and described in the literature. For this preparation, two different processes may be envisaged according to the nature of the organic solvent. When the organic solvent is water-immiscible, the hydrogen peroxide is extracted, with vigorous stirring, using an aqueous 60% hydrogen peroxide solution (200 volumes). After stirring from 3 to 8 hours, the aqueous phase is saturated with sodium chloride and the organic phase is separated out by settling and then dried over sodium sulfate. When the organic solvent is water-miscible, the water is removed by azeotropic distillation.

For example, acetonitrile, tert-butanol, cyclohexane, heptane, pentane, 1,2-dichloroethane or ethyl acetate can be used as co-solvent capable of forming an azeotropic mixture with water.

The azeotropic entrainment of the water can take place at the boiling point of the mixture. After cooling, drying is performed over anhydrous sodium sulfate.

The titre of the hydrogen peroxide in the organic solvent can be determined by polarography.

Depending on the nature of the solvent, the hydrogen peroxide content of the compositions may vary within a wide range.

As azeotropic distillation process, reference may be made for example to document EP 121 660.

When composition (B) contains hydrogen peroxide, its concentration may range from 1% to 50%, for example, from 4% to 30%, such as from 4% to 20%, for instance, from 5% to 15% by weight relative to the weight of composition (B).

The anhydrous hydrogen peroxide composition may also contain other ingredients, for example products for increasing the viscosity, in order to, for example, avoid any flow of the composition during application.

It may also contain various adjuvants usually used in cosmetics, for instance surfactants, for example nonionic or anionic surfactants and thickeners.

For example, it may contain at least one fatty substances not containing any carboxylic acid functional groups, as defined previously, either as solvent(s) for the hydrogen peroxide and/or the hydrogen peroxide precursors, or as additional compounds.

As indicated previously, the dyeing/bleaching agent obtained from composition (A) and anhydrous composition (B) is such that the at least one fatty substance is present in the mixture of the two compositions in an amount greater than or equal to 20% by weight relative to the total weight of the mixture of these two compositions.

Thus, the at least one fatty substance not containing any carboxylic acid functional groups may be present in composition (A) or composition (B), or simultaneously in both compositions, provided that the total amount of the at least one fatty substance in the mixture of compositions (A) and (B) is at least equal to 20% by weight relative to the total weight of the mixture of the two compositions (A) and (B).

For example, the total amount of the at least one fatty substance not containing any carboxylic acid functional groups in the mixture of compositions (A) and (B) represents at least 25% by weight, such as at least 30% by weight relative to the total weight of the said mixture.

The total amount of the at least one fatty substance not containing any carboxylic acid functional groups in the mixture of compositions (A) and (B) is for example, less than or equal to 90% by weight, such as less than or equal to 70% by weight relative to the total weight of the said mixture.

In at least one embodiment of the disclosure, the agent of the disclosure is formed only from the two compositions (A) and (B).

Another aspect of the present disclosure is a process for dyeing and/or bleaching keratin fibers, comprising the application to the said keratin fibers of the agent as described above.

According to the disclosure, the agent applied to keratin fibers results from the mixing of composition (A) and anhydrous composition (B), this mixing being performed either before application to keratin fibers (extemporaneous preparation) or directly on the keratin fibers (successive application to the fibers of composition (A) and of anhydrous composition (B) without intermediate rinsing).

Thus, according to at least one embodiment of the process according to the disclosure, composition (A) and anhydrous composition (B) are applied to the wet or dry keratin fibers, successively and without intermediate rinsing.

According to at least one embodiment of the process according to the disclosure, a composition obtained by extemporaneously mixing, before application, composition (A) and anhydrous composition (B) is applied to the wet or dry keratin fibers.

In this case, the interval between the mixing of composition (A) and of anhydrous composition (B) and the application of the mixture to the hair does not exceed, for example 30 minutes, for example, 10 minutes such as five minutes.

The weight ratio of the amount of composition (A) used to the amount of anhydrous composition (B) used may range from 0.2 to 50, for example, from 0.3 to 10, such as from 0.3 to 1.

In addition, the mixture present on the fibers (resulting either from the extemporaneous mixing of composition (A) and of anhydrous composition (B) or from the successive application thereof) is left on for a time generally from one minute to one hour, for example, from five minutes to 30 minutes.

The temperature during the process ranges, for example, from room temperature (e.g. from 15 to 25° C.) to 80° C., such as from room temperature to 60° C.

After the treatment, the keratin fibers can optionally be rinsed with water, optionally undergo washing with a shampoo followed by rinsing with water, and are then dried or left to dry.

Still another aspect of the disclosure is a multi-compartment dyeing and/or bleaching "kit", comprising a first compartment comprising a composition (A), and also a second compartment comprising an anhydrous composition (B), compositions (A) and (B) being as described above.

This kit may also comprise at least one composition for washing and/or conditioning keratin fibers, which can be intended to be applied before and/or after the dyeing and/or bleaching treatment according to the disclosure.

The examples that follow serve to illustrate the disclosure without, however, being limiting in nature.

EXAMPLES

Example 1

The following compositions were prepared:
The direct emulsion A1 below was prepared according to a phase inversion temperature (PIT) process:
Manufacturing Process
1—Phase A was heated on a water bath with stirring using a Rayneri blender (400 rpm). A white emulsion, which became translucent at about 68° C. (through a microemulsion phase) and which thickened beyond that temperature, was obtained.
2—Once the emulsion thickened, the water bath was removed and the emulsion was allowed to cool with continued stirring.
3—The gelling agent (carbopol) was introduced at about 50° C.
4—The ethanol, the monoethanolamine, the dyes, the ascorbic acid and the chelating agent, were introduced to the emulsion at room temperature, and the water lost on evaporation (<5%) was readjusted.

A translucent gelled emulsion with a droplet size <1 μm was then obtained.

Coloring Composition A1

| Phase | Name | g % |
|---|---|---|
| A | Beheneth-10 | 6.00 |
| | glycerol | 9.00 |
| | ethylhexyl palmitate | 17.70 |
| | liquid petroleum jelly | 45.00 |
| | water | 16.00 |
| B | carboxyvinyl polymer synthesized in an ethyl acetate/cyclohexane mixture (Carbopol 980) | 0.30 |
| C | ethanol | 2.00 |
| | monoethanolamine | 4.00 |
| | diethylenetriaminepentaacetic acid | 0.015 |
| | ascorbic acid | 0.25 |
| | 1-methyl-2,5-diaminobenzene | 0.14 |
| | 1-hydroxy-4-aminobenzene | 0.17 |
| | resorcinol | 0.08 |
| | 1-methyl-2-hydroxy-4-β-hydroxyethylaminobenzene | 0.21 |
| | 1-methyl-2-hydroxy-4-aminobenzene | 0.23 |

Oxidizing Compositions:

| Composition B1 (powder) | |
|---|---|
| Oxidizing composition (g %) | B1 |
| Urea peroxide | 90 |
| Lactose | 10 |

| Composition B2 (liquid) | |
|---|---|
| Oxidizing composition (g %) | B2 |
| Hydrogen peroxide | 15 |
| Polytetrahydrofuran dimethyl ether | 85 |

At the time of the use, composition A1 was mixed with an anhydrous composition (B1) or (B2) in the following proportions:
1 part of composition A1 with 0.1 part of oxidizing composition B1
1 part of composition A1 with 0.25 part of oxidizing composition B2

The mixtures were then applied to locks of grey hair containing 90% white hairs. After a leave-on time of 30 minutes at room temperature (25° C.), the hairs were rinsed, washed with a standard shampoo and then dried. A mahogany-blonde coloration was obtained.

What is claimed is:
1. An agent for dyeing and/or bleaching keratin fibers, comprising:
composition (A) comprising at least one basifying agent, and anhydrous composition (B) comprising hydrogen peroxide and/or at least one hydrogen peroxide precursor, wherein composition (A) and/or composition (B) comprise at least one fatty substance not containing any carboxylic acid functional groups, such that the total amount of the at least one fatty substance not containing any carboxylic acid functional groups is present in the mixture of composition (A) and composition (B) in an amount greater than 20% by weight.

2. The agent according to claim 1, wherein the at least one basifying agent is chosen from aqueous ammonia, alkali metal carbonates, alkanolamines and derivatives thereof, sodium hydroxide, potassium hydroxide, and the compounds of formula (I) below:

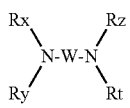

(I)

wherein W is a $C_1$-$C_6$ alkylene residue optionally substituted with a hydroxyl group or a $C_1$-$C_6$ alkyl radical; Rx, Ry, Rz and Rt, which may be identical or different, are chosen from a hydrogen atom, a $C_1$-$C_6$ alkyl, $C_1$-$C_6$ hydroxyalkyl and $C_1$-$C_6$ aminoalkyl radicals.

3. The agent according to claim 2, wherein the at least one basifying agent is chosen from alkanolamines.

4. The agent according to claim 1, wherein composition (A) contains at least 25% by weight of at least one oil not containing any carboxylic acid functional groups, relative to the total weight of composition (A).

5. The agent according to claim 4, wherein composition (A) contains at least 30% by weight of at least one oil not containing any carboxylic acid functional groups, relative to the total weight of composition (A).

6. The agent according to claim 1, wherein the at least one fatty substance not containing any carboxylic acid functional groups is chosen from $C_6$-$C_{16}$ lower alkanes, non-silicone oils of mineral, plant, animal or synthetic origin, fatty alcohols, fatty acid esters, fatty alcohol esters, non-silicone waxes and silicones.

7. The agent according to claim 1, wherein the at least one fatty substance not containing any carboxylic acid functional groups is a compound that is liquid at 25° C. and at atmospheric pressure.

8. The agent according to claim 7, wherein the at least one fatty substance is chosen from liquid paraffins, liquid petroleum jelly, polydecenes, and liquid esters of fatty acids and fatty alcohols.

9. The agent according to claim 8, wherein the fatty substance is liquid petroleum jelly.

10. The agent according to claim 1, wherein the amount of water in composition (A) ranges from 5% to 90% by weight relative to the weight of composition (A).

11. The agent according to claim 10, wherein the amount of water in composition (A) is present in an amount ranging from 10% to 80% by weight relative to the weight of composition (A).

12. The agent according to claim 1, wherein composition (A) comprises at least one oxidation dye chosen from oxidation bases, and optionally combined with at least one coupler.

13. The agent according to claim 1, wherein composition (A) comprises at least one direct dye.

14. The agent according to claim 1, wherein composition (B) is in the form of a powder, a paste, a cream, a thickened liquid, or unthickened liquid.

15. The agent according to claim 1, wherein the hydrogen peroxide precursor is chosen from polymer/hydrogen peroxide complexes, urea peroxide, alkali metal or alkaline-earth metal perborates, and alkaline-earth metal or alkaline-earth metal carbonates.

16. The agent according to claim 1, wherein the agent further comprises at least one organic solvent.

17. The agent according to claim 16, wherein the at least one organic solvent of composition (B) is chosen from fatty substances not containing any carboxylic acid functional groups, at least partially water-soluble alcohols, acyclic polyols, acyclic polyol ethers and polytetrahydrofuran ethers.

18. The agent according to claim 1, wherein the total amount of at least one fatty substance not containing any carboxylic acid functional groups, represents at least 25% by weight relative to the total weight of the mixture of composition (A) and composition (B).

19. The agent according to claim 18, wherein the total amount of at least one fatty substance not containing any carboxylic acid functional groups, after mixing at least one composition (A) and the at least one anhydrous composition (B), represents at least 30% by weight relative to the total weight of the mixture of these two compositions.

20. A process for dyeing and/or bleaching keratin fibers, comprising applying to the fibers, which can be wet or dry fibers,
composition (A) comprising at least one basifying agent, and
anhydrous composition (B) comprising hydrogen peroxide and/or at least one hydrogen peroxide precursor,
successively and without intermediate rinsing,
wherein composition (A) and/or composition (B) comprise at least one fatty substance not containing any carboxylic acid functional groups, such that the total amount of the at least one fatty substance not containing any carboxylic acid functional groups after mixing composition (A) and composition (B) is greater than 20% by weight.

21. A process for dyeing and/or bleaching keratin fibers, comprising:
mixing extemporaneously
composition (A) comprising at least one basifying agent, and
anhydrous composition (B) comprising hydrogen peroxide and/or at least one hydrogen peroxide precursor to form a mixture,
wherein composition (A) and/or composition (B) comprise at least one fatty substance not containing any carboxylic acid functional groups, such that the total amount of the at least one fatty substance not containing any carboxylic acid functional groups after mixing composition (A) and composition (B) is greater than 20% by weight; and,
applying the mixture to the fibers, which can be wet or dry fibers.

22. A multi-compartment dyeing and/or bleaching kit, comprising
at least one first compartment comprising composition (A) comprising at least one basifying agent, and
at least one second compartment comprising anhydrous composition (B) comprising hydrogen peroxide and/or at least one hydrogen peroxide precursor,
wherein composition (A) and/or composition (B) comprise at least one fatty substance not containing any carboxylic acid functional groups, such that the total amount of the at least one fatty substance not containing any carboxylic acid functional groups after mixing composition (A) and composition (B) is greater than 20% by weight.

* * * * *